United States Patent [19]
Gilcher et al.

[11] Patent Number: 6,113,554
[45] Date of Patent: Sep. 5, 2000

[54] AUTOMATIC WHOLE BLOOD COLLECTION SYSTEM

[75] Inventors: Ronald O. Gilcher, Oklahoma City, Okla.; Jacques Chammas, Walpole, Mass.; Joseph M. Medberry, Seekonk, Mass.; Gary R. Stacey, Marshfield, Mass.

[73] Assignee: Haemonetics Corporation, Braintree, Mass.

[21] Appl. No.: 09/174,495

[22] Filed: Oct. 16, 1998

[51] Int. Cl.[7] .................................................. A61B 5/00
[52] U.S. Cl. ............................................. 600/573; 604/31
[58] Field of Search ............................... 600/562; 604/27, 604/3, 30, 4, 43, 65–67, 93, 122, 151

[56] References Cited

U.S. PATENT DOCUMENTS

| | | | |
|---|---|---|---|
| 4,316,466 | 2/1982 | Babb | 604/31 |
| 4,385,630 | 5/1983 | Gilcher et al. | 604/31 |
| 4,474,568 | 10/1984 | Schoendorfer et al. | 604/4 |
| 4,490,135 | 12/1984 | Troutner | 604/31 |
| 5,387,187 | 2/1995 | Fell et al. | 604/6 |

*Primary Examiner*—Max Hindenburg

[57] ABSTRACT

A whole blood collection system includes an automated pump/control unit and an accompanying disposable blood set. When combined and connected to a source of anticoagulant, these elements allow automatic priming of the blood set with anticoagulant and automatic collection of anticoagulated blood product according to three different collection modes. The unit's pump and the blood set are specially designed to cooperate during the collection process to assure that the collected product has a precise blood to anticoagulant ratio. During the collection procedure, the pump/control unit automatically collects data relating to the procedure. Additional data specifically identifying components of the blood set, such as the blood collection bag, along with identification data on the donor's registration form may be scanned into the pump/controller unit by a scanner associated with the unit; this facilitates positive sample identification and tracking. At the end of the procedure, a printer in the pump/controller unit automatically prints out this information so that a detailed record is immediately available about the collected blood product, the procedure for collecting it and the source of the product, i.e., the donor.

26 Claims, 4 Drawing Sheets

FIG. 1

AUTOMATIC WHOLE BLOOD COLLECTION SYSTEM

This invention relates to an automatic whole blood collection system. It relates more particularly to a method and apparatus for standardizing volumetric whole blood collection and red blood cell mass collection so that the collection process can be accomplished efficiently with minimum damage to the blood and with minimum discomfort to the donor.

BACKGROUND OF THE INVENTION

Prior systems for collecting blood rely on venous pressure and hydrostatic pressure to cause blood to flow from a donor's arm. A phlebotomy needle that is connected by tubing to a blood collection bag containing anticoagulant is inserted into a donor's arm. Hydrostatic pressure is achieved by positioning the collection bag about 18 inches below the level of the donor's arm and venous pressure is controllable to some extent by varying the pressure in a cuff attached to the donor's arm above the venipuncture site and, by directing the donor to alternately flex and relax his/her hand. Older collection apparatus used a relatively large needle (e.g., 16 gauge) which, when inserted, caused appreciable patient discomfort. Also, during the collection process, the non-anticoagulated whole blood drawn from the donor had to pass through the phlebotomy needle and along a length of tubing before it reached the anticoagulant in the blood collection bag. If the rate of flow of blood through the tubing was not maintained high enough, clotting could occur, reducing the usefulness of the collected blood.

To avoid the aforementioned problems, there has been developed relatively recently blood donation apparatus which utilizes a peristaltic or roller pump to withdraw whole blood from a donor through a much smaller (e.g., 19 gauge) phlebotomy needle, and to pump the blood through a tube leading to the collection bag. Anticoagulant flowing through a second tube leading from an anticoagulant source is mixed with the whole blood right at the outlet of the phlebotomy needle. The anticoagulant tube passes through the same pump head that draws the whole blood from the donor, so that the ratio of blood to anticoagulant is determined by the ratio of the diameter and elastic properties of the drawn blood tube with respect to those of the anticoagulant tube. Such a blood donation apparatus is disclosed in U.S. Pat. No. 4,385,630.

While that patented apparatus is a considerable improvement over the prior blood collection apparatus, it still has certain drawbacks. For example, it must be primed manually so that anticoagulant fills the anticoagulant tube down to the phlebotomy needle. Also, it employs a peristaltic pump with a single roller pump head acting on both the blood tube and anticoagulant tube. Therefore, the blood-to-anticoagulant ratio depends upon the tubing characteristics, making it difficult to change that ratio. Still further, the disposable blood collection set used in that prior blood donation apparatus is relatively difficult to install in the pump unit such that the drawn blood and anticoagulant tubes are properly positioned on the unit's pump head.

That patented blood donation apparatus is further disadvantaged because it is only able to collect a set volume of whole blood. Often, it is desirable to have the option of collecting different blood volumes. For example, in some cases, it may be necessary to collect a specific mass of red blood cells (RBC) based on the donor's known hematocrit, i.e., the percentage by volume of RBC in drawn whole blood. Even if the target volume of RBC is always the same in such cases, the volume of whole blood to be drawn will vary from donor to donor.

Finally, that known apparatus does not provide a record of the collection procedure and does not positively correlate the drawn blood with the donor of that blood. Therefore, there is always the possibility of the collected blood being misidentified and misused.

SUMMARY OF THE INVENTION

Accordingly, it is an object of the present invention to provide a fully automatic whole blood collection system.

Another object of the invention is to provide a collection system of this type which is self-priming.

A further object of the invention is to provide a system such this which is relatively easy to use.

Yet another object of the invention is to provide such a system which is programmable to allow the collection of different blood volumes.

Still another object of the invention is to provide a whole blood collection system which facilitates positive identification of the donor's blood and simplifies the keeping of records relating to the blood donations.

A further object of the invention is to provide a blood collection system which allows phlebotomists to draw blood safely and reliably from several donors in rapid succession.

Yet another object of the invention is to provide a disposable blood collection set for use in the above system.

A further object of the invention is to provide a method of tracking a donor's blood collected by the above whole blood collection system.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in the following detailed description, and the scope of the invention will be indicated in the claims.

Briefly, the whole blood collection system of the present invention comprises an automated pump/control unit and an accompanying disposable blood set. When combined and connected to a source of anticoagulant, these elements allow automatic priming of the blood set with anticoagulant and automatic collection of anticoagulated blood product according to three different collection modes to be described. As will be seen, the unit's pump and the blood set are specially designed to cooperate during the collection process to assure that the collected product has a precise blood to anticoagulant ratio, typically in excess of 5:1, e.g., 8:1.

During the collection procedure, the pump/control unit automatically collects data relating to the procedure. Additional data specifically identifying components of the blood set, such as the blood collection bag, along with identification data on the donor's registration form and on various blood samples may be scanned into the pump/controller unit by a scanner associated with the unit; this facilitates positive sample identification and tracking. At the end of the procedure, a printer in the pump/controller unit automatically prints out this information so that a detailed record is immediately available about the collected blood product, the procedure for collecting it and the source of the product, i.e., the donor. Thus, there is minimum likelihood of the product being mislabeled.

As will be seen, the system is easy to use and quite efficient so that the collection time is kept to a minimum, allowing a phlebotomist to draw blood safely and reliably from several donors in rapid succession with minimum discomfort to the donors.

BRIEF DESCRIPTION OF THE DRAWINGS

For a fuller understanding of the nature and objects of the invention, reference should be had to the following detailed description taken in connection with the accompanying drawings, in which:

FIG. 1 is an isometric view of an automatic whole blood collection system according to the invention;

DETAILED DESCRIPTION OF AN ILLUSTRATIVE EMBODIMENT

Figure 1:
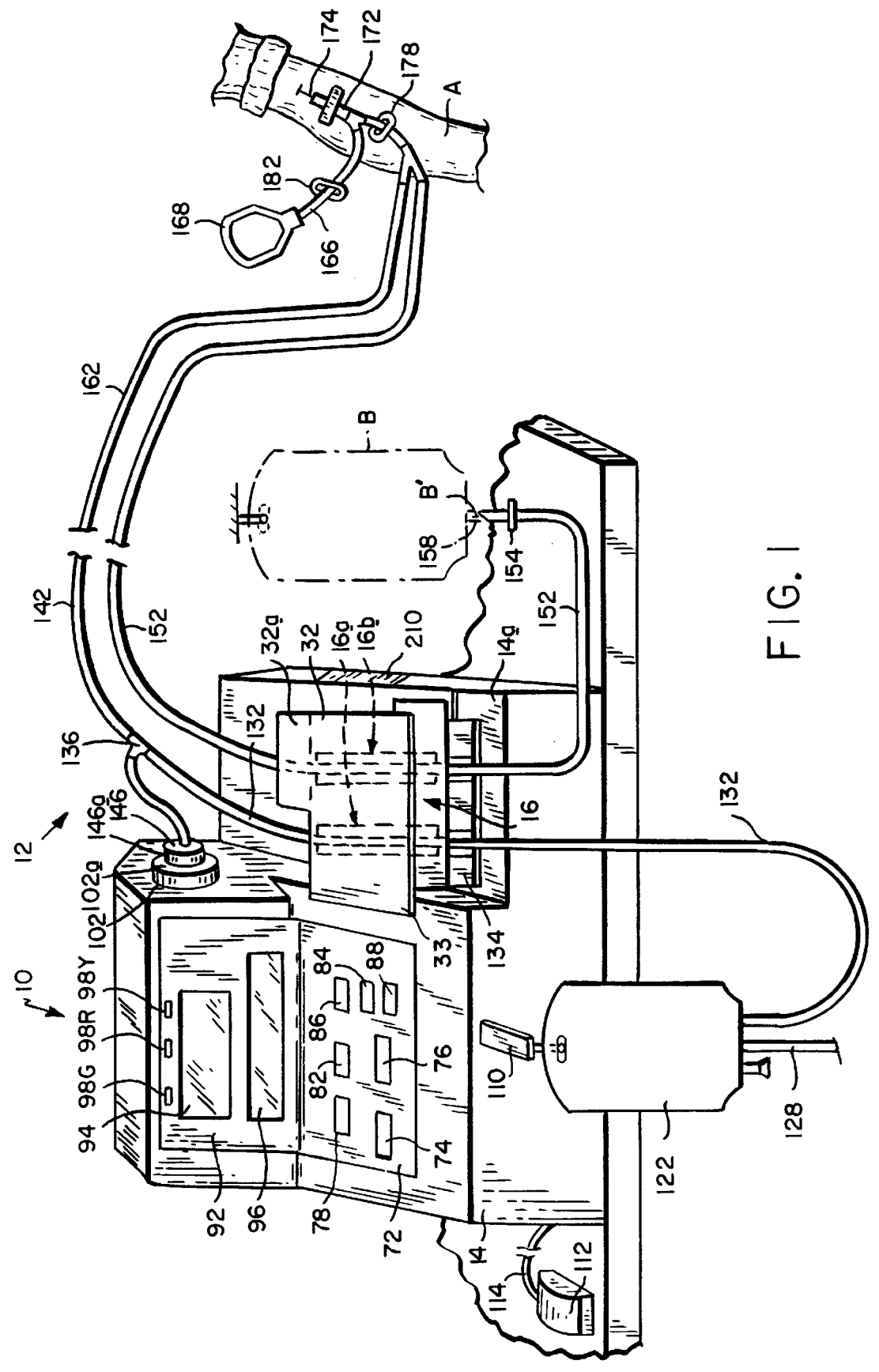
Figure 2:
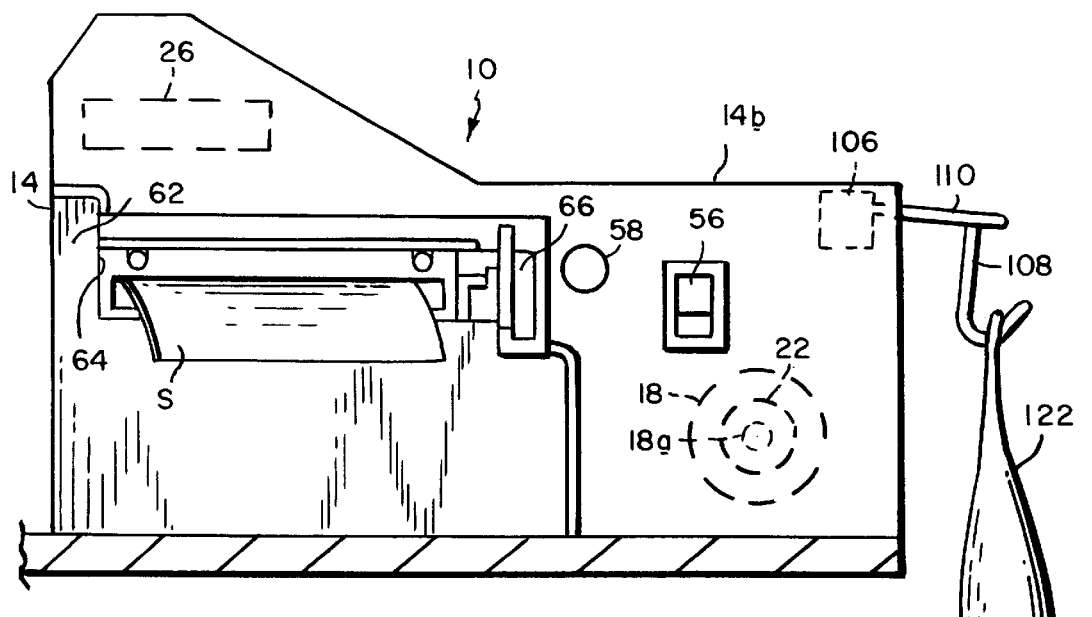
FIG. 2 is a right side elevational view of the FIG. 1 system's pump/control unit.
Figure 3:
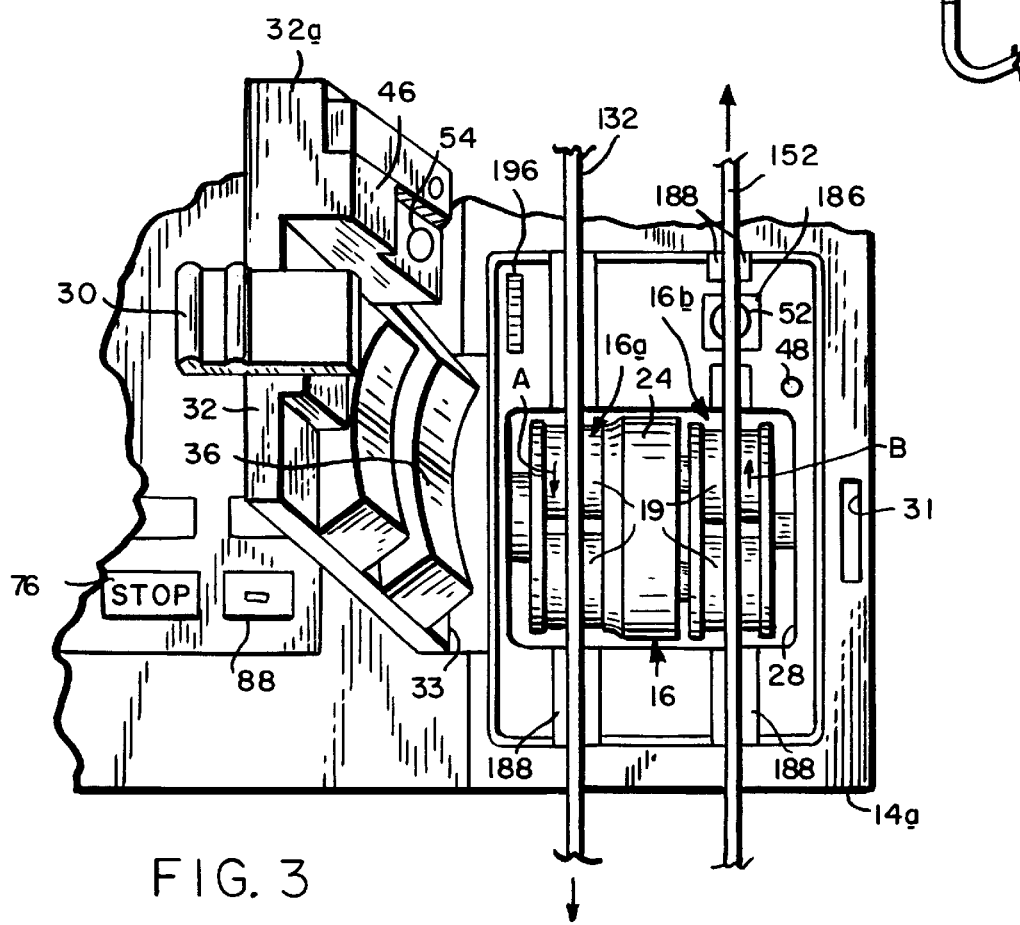
FIG. 3 is a fragmentary top plan view of the FIG. 2 unit showing the unit's pump platen in its open position.
Figure 5:
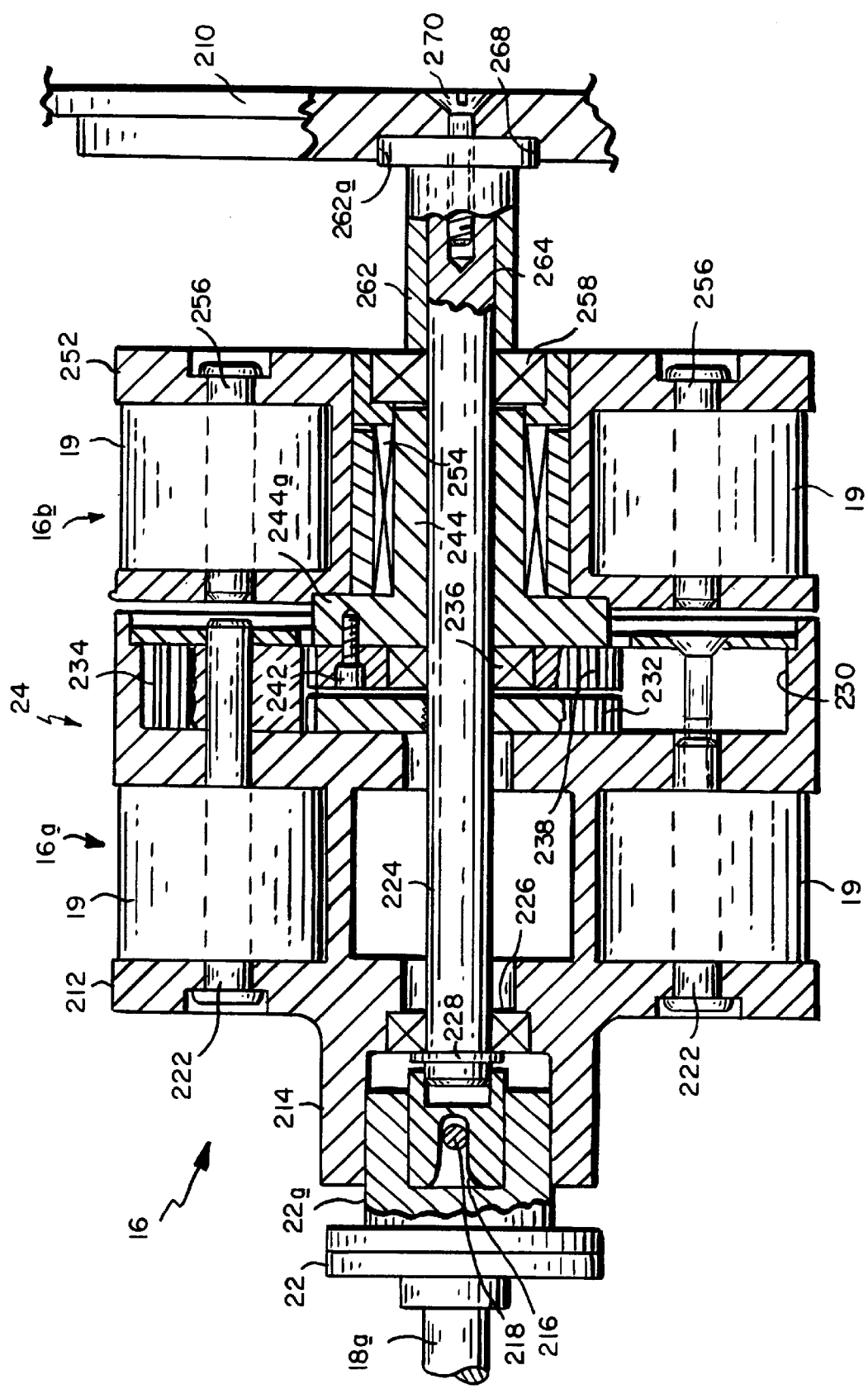
FIG. 5 is a longitudinal sectional view with parts broken away on a larger scale showing the peristaltic pump in the FIG. 2 unit in greater detail.

Referring to FIGS. 1 to 3 of the drawings, the whole blood collection system comprises a pump/control unit shown generally at 10 and a disposable blood collection set indicated generally at 12. As shown in those figures, unit 10 includes a housing 14 which houses a special peristaltic pump shown generally at 16 and driven by the shaft 18a of an electric motor 18 by way of a one-way clutch 22 (FIGS. 2 and 5).

As best seen in FIG. 3, pump 16 has two rotary heads 16a and 16b, each head being constituted by four rollers 19.

The two pump heads 16a and 16b are mechanically coupled together by means of a speed reducer and rotation reverser 24 so that when head 16a is rotated by motor 18 in the direction of arrow A, the pump head 16b will rotate in the opposite direction, i.e., in the direction of the arrow B, at a slower rate. In accordance with the invention, the gear ratio of speed reducer 24 is selected so that the ratio of the speeds of heads 16a and 16b is the same as the desired ratio of blood to anticoagulant in the blood being drawn from a donor by this system, a typical ratio being in excess of 5:1, e.g., 8:1. Thus, the ratio of blood to anticoagulant can be changed simply by substituting a different speed reducer 24 having the desired gear reduction ratio.

The motor 18 that drives pump 16 is preferably a 28 volt DC motor energized by voltage from a standard AC/DC converter (not shown) which may be plugged into a suitable electrical outlet. Motor 18 is controlled by a controller 26 located in housing 14 as shown in FIG. 2.

Pump 16 is positioned in housing 14 so that one or two rollers of each head 16a and 16b are exposed through an opening 28 in a top wall 14a of housing 14. As shown at FIGS. 1 and 3, a platen 32 is connected by a hinge 33 to the housing top wall 14a so that the platen can swing between a closed position shown in FIG. 1 wherein the platen overlies pump 16 and closes the opening 28, and an open position illustrated in FIG. 3 wherein the platen is swung away from opening 28 (thereby exposing the pump heads 16a and 16b). The platen may be releasably retained in its closed position by the engagement of a latch 30 pivotally mounted to the platen in a keeper 31 present in housing top wall 14a adjacent opening 28 therein.

As best seen in FIG. 3, the underside of platen 32 has protruding undersurface areas 34a and 34b which are curved to accommodate the rotational movements of the pump heads 16a and 16b, respectively. When the platen 32 is in its closed position shown in FIG. 1, the undersurface areas 34a and 34b extend through opening 28 and are spaced opposite the uppermost roller(s) 19 of the pump heads 16a and 16b, respectively, a distance less than the diameter of the tubing comprising the blood collection set 12. Resultantly, when tubing segments are positioned on the pump heads 16a and 16b as shown in FIG. 3, and the platen 32 is closed, energizing motor 18 causes each pump head to produce a rolling pinch which pumps fluid through the associated tubing in the direction of the corresponding arrow A or B. The one-way clutch 22 assures that the pump heads can only rotate in the directions of those arrows.

As shown on FIG. 3, the platen 32 has a side extension 32a which extends to the rear of housing 14 and overlies the housing top wall 14a. The undersurface of the side extension 32a has a pad 46 which, when the platen is closed as in FIG. 1, engages and closes a proximity switch 48 projecting through the housing top wall 14a adjacent to opening 28 therein. Switch 48 provides an interlock. Unless the controller 26 detects that switch 48 is closed (indicating that platen 32 is closed and latched), the controller will not activate motor 18.

Also mounted in the housing top wall 14a just behind pump head 16b is a sonic emitter/detector 52. A second similar emitter/detector 54 is mounted in the underside of platen side extension 32a adjacent pad 46. When tubes are positioned on the pump heads 16a and 16b as shown in FIG. 3 and platen 32 is closed, the two emitter/detectors 52, 54 are located respectively above and below the tube on pump head 16b. Thus, each device 52, 54 is positioned to receive the acoustic signals produced by the other after they have passed through that tube. The received signals from the two devices 52, 54 are compared by controller 26 to detect the presence and absence of fluid, i.e., blood, in that tube. In fact, the emitter/detectors 52, 54 are accurate enough to detect microbubbles, but are calibrated for bubbles as small as 0.3 inch at a pump 16 speed of 100 RPM. The controller 26 is programmed to deactivate pump motor 18 in the absence of fluid in the tube on pump head 16b.

As shown in FIGS. 1 and 2, various controls are mounted in housing 14 to control the operation of the pump/control unit 10. More particularly, there is an ON/OFF power switch 56 mounted in the right side wall 14b of housing 14. Next to switch 56 is a PAPER LOAD button 58 which, when actuated, allows the removal of a digital thermal printer 62 from the side of housing 14 in order to load paper into the printer. Printer 62 prints blood collection data as alphanumeric characters and bar codes on a paper strip S which issues from a slot 64 in the printer. The printer also has a paper feed knob 66 which may be turned to advance the paper strip S, e.g., when loading paper into the printer.

The pump/control unit 10 also includes a control panel 72 located at the front of the housing and containing several control buttons. A START button 74 starts unit 10 at the beginning of the blood collection process, and a STOP button 76 can be depressed to stop the collection process at any point in the collection cycle. At the end of the cycle, controller 26 causes printer 62 to automatically print out data relating to that procedure. Also, a PRINT button 78 may be used to activate printer 62 to print more copies of the data, and a MUTE button 82 quiets the audible alarms (not shown) built into unit 10. Panel 72 also has a set of three related buttons, namely, a MODE button 84, a "+" button 86 and a "−" button 88. These buttons are used to enter a donor's hematocrit or the targeted blood collection volume before the start of a collection procedure, as will be described in detail later. The closing of each of the aforementioned switches and control buttons is detected by controller 26, which is programmed to control the operation of the various elements of unit 10 in the manner to be described.

Referring now to FIG. 1, the pump/control unit 10 has, in addition, several displays mounted in a display panel 92, which projects up behind control panel 72. The display panel includes a numeric display 94 which displays the blood volume collected by unit 10. A second display 96 displays two lines of alphanumeric characters and is used to deliver user messages. There are also three LEDs located above display 94, i.e., a green LED 98G, a red LED 98R and a yellow LED 98Y. These lights are used as indicators of the operating conditions of unit 10 as will be described. All of the displays are controlled by controller 26.

Unit 10 also includes a pressure detector 102 which has an inlet nipple 102a and which is mounted to housing 14 adjacent to display panel 92 as shown in FIG. 1. As will be described in more detail later, when unit 10 is in operation, detector 102 monitors the donor's blood pressure in the blood line from the donor to the collection system. The controller 26 monitors feedback signals from the transducer and controls the speed of the pump motor 18 in order to maximize the blood flow while keeping the pressure level at a value that ensures the donor's comfort. Controller 26 may be programmed to limit pump head 16a to a maximum speed of, say, 100 RPM, so that in a typical collection procedure, about 75–80 ml of anticoagulated blood will be drawn through the tubing on that pump head.

The pump/control unit 10 has, in addition, an electronic weigher 106. The weigher may comprise a transducer (e.g., piezoelectric bender, strain gauge, etc.) which produces an electrical output or value sampled by controller 26 and which represents the weight of a blood bag hanging on a hook 108 at the end of a lever arm 110 projecting from the front of housing 14 (see FIGS. 1 and 2). As will be described later, the output of the weigher 106 is used to determine the volume of the collected blood product.

Preferably, also, the pump/control unit 10 is provided with a hand-held bar code scanner 112 connected by a cable 114 to controller 26 as shown in FIG. 1. The scanner 112 is used to scan bar codes printed on the donor's registration form and on components of the blood collection set 12 and on blood samples for entry into the controller's memory in order to track the donor, the collected blood product and any test samples taken during the collection procedure.

Figure 4:
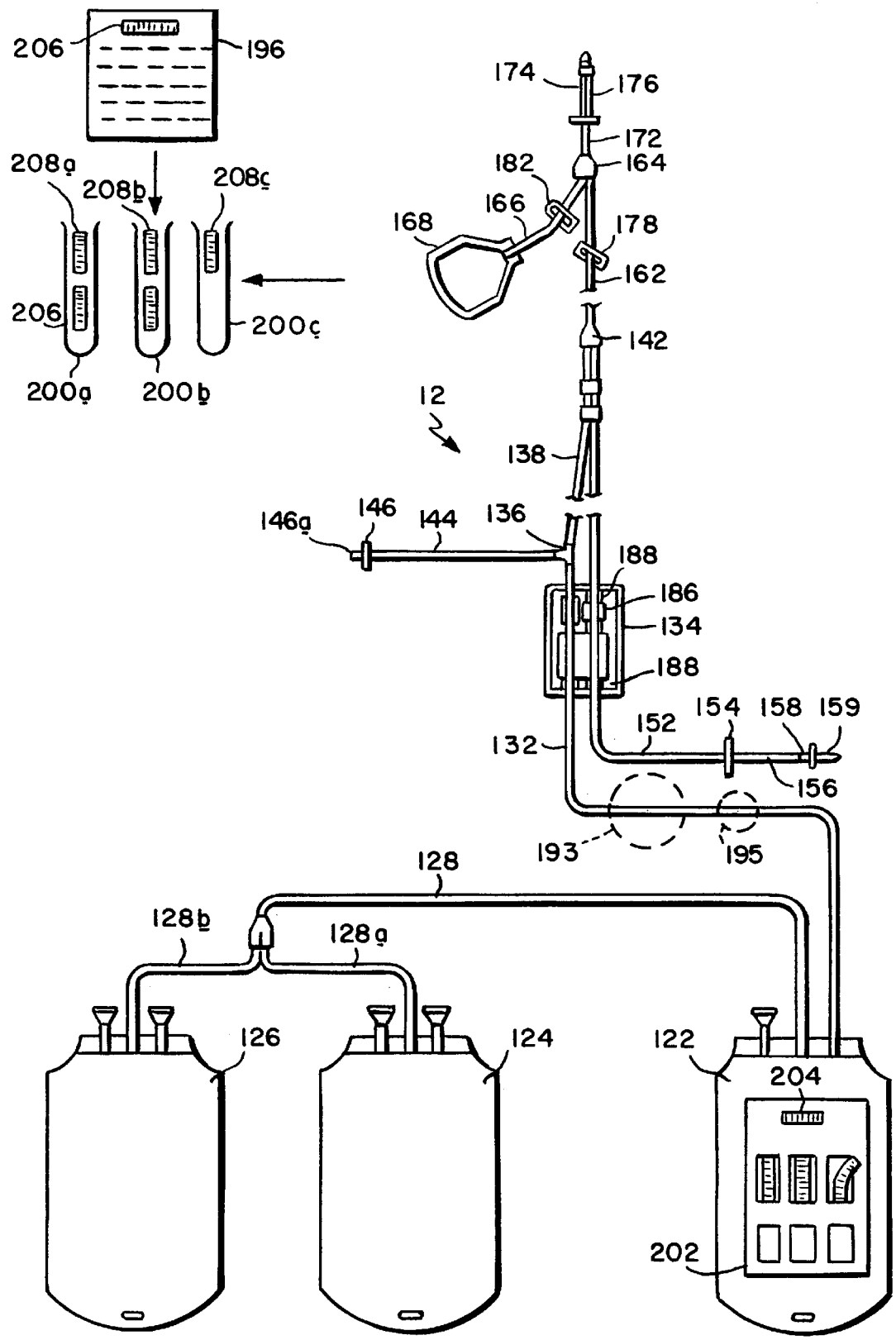
FIG. 4 is a plan view of the FIG. 1 system's disposable blood collection set.

Turn now to FIG. 4 which shows in detail the various elements of the disposable blood collection set 12. The set 12 includes a main collection bag 122 and two satellite bags 124 and 126. Bag 122 may have a volume of 600 ml, for example, and be used to collect whole blood or RBC, while the two satellite bags 124 and 126 may each have a volume of 400 ml and be used to collect platelets and plasma, respectively. The bags are interconnected by a tube 128 leading from bag 122 and splitting into branches 128a and 128b leading to bags 124 and 126, respectively. Preferably, there is a breakable seal (not shown) in tube 128 to prevent transfer of fluid between bag 122 and bags 124 and 126 during storage and shipment.

The disposable set 12 also has a tube 132 extending from bag 122 over a tubing tray 134 to one arm of a T-connection 136. Tube 132 communicates at connection 136 with a tube 138 which leads to a Y-connection 142. The leg of the T-connection 136 connects to one end of a length of tubing 144 which extends to the outlet side of an antibacterial filter 146 (e.g., 0.22μ) which prevents infiltration of contaminants into set 12. Filter 146 has an inlet luer 146a adapted to be coupled to the nipple 102a of the pressure sensor 102 on unit 10 as illustrated in FIG. 1.

Tray 134 also supports an anticoagulant tube 152 which extends from the Y-connection 142 to the outlet of an antibacterial filter 154 (e.g., 0.22μ). The filter inlet is connected via tubing 156 to a tubular spike 158 which is adapted to be coupled to the spike port B' of a bag B containing anticoagulant as shown in phantom in FIG. 1. Prior to using set 12, the spike 158 may be protectively enclosed in a sheath 159. The leg of Y-connection 142 is connected to a tube 162 which leads to one branch of a second Y-connection 164, the other branch of which is connected via a tube 166 to a small pre-sample pouch 168. This pouch allows the collection of a sample of a donor's blood without a separate venipuncture. The leg of connector 164 is connected by a short length of tubing 172 to a small (i.e., 18 or 19 gauge) phlebotomy needle 174 with a back-eye. Preferably, needle 174 is protected by a cap 176 prior to use. Preferably also, the tubes 162 and 166 are provided with clamps 178 and 182, respectively, for reasons that will become apparent.

Still referring to FIG. 4, the tubing tray 134 of the blood set 12 is a generally rectangular card-like element preferably made of plastic. It is provided with a relatively large rectangular window 184 and a smaller similarly shaped window 186 adjacent to window 184. The tray is formed with sets of closely spaced parallel ribs 188 which are adapted to capture the blood tube 132 and the anticoagulant tube 152 so that the segments of those tubes overlying tray 134 are straight and parallel to one another and such that the tube 132 segment bridges opening 184 and different portions of the tube 152 segment bridge opening 184 and opening 186. The tubes may be retained between their respective sets of ribs 188 by friction and compression forces. Alternatively, the tubes may be bonded or heat sealed in place.

If desired, set 12 may be provided with components to facilitate initial filtration or processing of drawn blood. For example, as shown in phantom in FIG. 4, a blood centrifuge bowl 193 may be interposed along tubing 132, allowing the anticoagulated blood to be separated into its components; see e.g., U.S. Pat. No. 5,387,187, the contents of which is hereby incorporated herein by reference. Also, an in-line filter 195 for white blood cells or platlets may be disposed before or after the bowl 193 as shown in that same figure.

Prior to use, the disposable blood set 12 may be packaged in a suitable sterile pouch or bag (not shown).

In order to operate the system, unit 10 is turned on via switch 56 and the desired collection mode is selected by depressing MODE button 84. Thereupon, the unit performs various diagnostic tests to ensure that the unit's displays and systems are operating properly according to a routine programmed into controller 26. If any of the tests fails, an action message will be displayed by display 96, thereby prompting appropriate corrective action. When the self testing is completed, unit 10 will indicate its readiness to accept disposable set 12 by displaying in display 96, "PLEASE INSTALL DISPOSABLE."

The controller 26 in the pump/control unit 10 is programmed for three collection modes selected by successively depressing the MODE button 84 after unit 10 is powered up as aforesaid. A STANDARD mode represents the default mode at power up; in accordance therewith, display 96 will indicate "STANDARD MODE," a target volume of 450 ml and its equivalent of 513 ml of anticoagulated blood. When operating in this ode, the system will collect a set volume (i.e., 450 ml) of whole blood, mix it with antioagulant at an 8:1 ratio (i.e., a volume of 63 ml), and then stop automatically.

If button 84 is depressed once, unit 10 switches to a VOLUME mode operation whereby the system collects a predetermined volume of fresh blood over a range of 50 to 500 ml, mixes it with anticoagulant at an 8:1 ratio and then stops automatically. During VOLUME mode operation, display 96 may initially show a default target volume of 450 ml for the fresh blood and its equivalent of 513 ml of anticoagulated blood. The target volume (as displayed) may be increased or decreased in 10 ml increments by depressing the "+" button 86 or the "−" button 88, and the displayed volume of the anticoagulated blood will increase or decrease accordingly.

When button 84 is depressed twice at power up, unit 10 operates in a RED CELL mode during which the system collects whole blood equivalent to a selected volume, e.g., 180 ml, of concentrated RBC, mixes the whole blood with anticoagulant at an 8:1 ratio and then stops automatically. In this mode, display 96 will show "RED CELL MODE" and display initially "40% HEMATOCRIT." In this mode, the default 40% hematocrit value may be increased by 1% each time the "+" button 86 is depressed and decreased 1% each time the "−" button 88 is depressed. When the displayed hematocrit matches the already known donor's hematocrit, depression of the STOP button 74 will enter that value into the controller 26 memory. Based thereon, display 96 will display the calculated target volume of anticoagulated blood based on the donor's hematocrit and 180 ml of RBC.

After mode selection and testing and when signaled to do so by display 96 as described above, the collection set 12 may be installed in unit 10 as shown in FIG. 3. More particularly, set 12 is removed from its sterile pouch and with clamps 178 and 182 closed, the bag 122 component of the set is hung from scale hook 108. Then, the platen 32 of unit 10 is opened and the tubing tray 134 positioned on the housing top wall 14a as shown in FIG. 3 such that the segments of tubes 132 and 152 on tray 134 are centered, and lay flat, on the pump heads 16a and 16b, respectively, and so that the portion of tube 152 bridging window 186 on the tray is centered on the acoustic detector 52.

The platen 32 is then closed and latched so as to clamp the tubing in the tray opening 128 between the pump heads 16a and 16b and the platen surfaces 36a and 36b. When the platen is latched, the platen pad 46 presses down on the tray, thereby depressing the proximity switch 48 which signals the controller 26 that pump 16 is properly loaded and latched.

Next, the inlet luer 146a of filter 146 is coupled to the inlet nipple 102a of the pressure sensor 102.

When set 12 is installed in unit 10 as aforesaid, unit 10 will indicate its readiness to start an autoprime sequence to prime set 12 by displaying on display 94 the message "000 ml" and displaying on display 96 the words "CLAMP NEEDLE—PRESS START TO PRIME." At this point, the operator may insert the spike 158 of set 12 into the port B' of the anticoagulant bag B as shown in FIG. 1, close clamp 178 and press the START button 74. Display 196 will now indicate the priming mode by displaying the word "PRIMING." During priming, the green LED 98G will be illuminated and controller 26 will activate the pump motor 18 causing the pump heads 16a and 16b to rotate respectively in the direction of the arrows A and B in FIG. 3. The pump head 16b will draw anticoagulant from bag B through filter 154 and along the anticoagulant tube 152 so that the fluid passes over detector 52. Once that detector detects the anticoagulant in tube 152, controller 26 will cause motor 18 to rotate the pump 16 a predetermined number of revolutions and then stop. This number of pump revolutions is enough to prime the set 12 with anticoagulant fluid up to the Y-connection 142 where the blood tube 132 and anticoagulant tube 152 merge.

During this priming sequence, the display 94 will indicate "000 ml" collected volume, although the pump 16 is rotating. If the sonic emitter/detectors 52, 54 do not detect anticoagulant in the tube 152, controller 26 will stop pump 16 automatically after the pump has completed a further predetermined number of revolutions. A message will thereupon appear on display 96 to indicate that anticoagulant has not been detected in tube 152.

On other hand, when the blood collection set 12 is properly primed, the display 96 will indicate that the system is ready to collect a donor's blood by displaying the message "READY" and the estimated collection time (e.g., "EST. TIME 8:00") on display 96 while display 94 will show "000 ml."

At this point, the cap 176 may be removed from the phlebotomy needle 174 and the needle inserted into the donor's arm A as shown in FIG. 1. Then, the clamp 178 may be released from tube 162, allowing blood to flow from the donor's arm along tube 162 whereupon it mixes with anticoagulant at the Y-connection 142. If it is desired to collect a sample of the donor's blood before the release of clamp 178, the clamp 182 may be released from the tube 166 leading to the sample pouch 168, allowing fresh blood to flow into that pouch until it is full, following which clamp 182 is closed on tube 166. As noted above, the pouch 168 allows a sample of the donor's blood to be taken without a separate venipuncture. Pouch 168 should remain clamped off during the entire blood collection process.

The system is now ready to collect the donor's blood. For purposes of the following description, we will assume that unit 10 is operating in its STANDARD mode. Collection is initiated by pressing the START button 74 on unit 10. At start, the controller 26 is programmed to cause motor 18 to rotate pump 16 and accelerate it until the pump reaches a steady state that causes blood to flow along tubes 162, 138 and 132 to collection bag 122. This steady state is defined as the pump velocity when the pressure detected by the pressure sensor 102 falls within the limits that provide for maximum flow with maximum donor comfort. During acceleration, the yellow LED 98Y will flash. When the pump 16 reaches a steady state, LED 98Y will turn off and three green LED 98G will flash once per revolution of pump head 16a to indicate that the pump is working. If the pressure level remains normal, the pump will continue to draw blood and stop automatically when the collected volume of anticoagulated blood in bag 122 reaches the selected volume, e.g., 513 ml. The operator can manually stop the collection procedure at any time by pressing the STOP button 76 on control panel 72.

During collection, the display 94 provides a real time display of the instantaneous volume of the collected anticoagulated blood. This information is obtained from the weigher 106, which is constantly weighing bag 122 as it is being filled. The signals from the weigher are processed by controller 26 to produce equivalent volume data used to control the pumping time of pump 16 and the information displayed by display 94. Also, the display 96 indicates the elapsed time since the pump 16 started to draw anticoagulated blood as well as the estimated time remaining to end the procedure. For example, that display may show the words "ELAPSED 4:12—REMAINING 3 MIN."

If unit 10 should be stopped manually by the operator depressing the STOP button during the collection procedure before the system has collected 513 ml of the blood product, the display 96 will indicate that the system is ready to continue collection of blood by displaying "<START> TO CONT." The volume count displayed by display 94 will remain at its present level and cannot be reset to zero. Also, the green LED 98G will stop flashing and the yellow LED 98Y will be turned on and the digits in the display 94 will flash to indicate that the pump 16 has stopped.

If the pump 16 should stop automatically for any safety reason (before collecting the set volume of product, i.e., 513 ml), the red LED 98R will be turned on and a message will appear on display 96 to guide the operator.

When the collection procedure is completed, display 94 will flash the collected volume number and display 96 will indicate the elapsed time for the procedure. If the procedure ends in 6 minutes and 35 seconds, for example, display 94 will flash 513 ml (representing 450 ml of the donor's blood plus 63 ml of anticoagulant fluid) and the display 96 will display the message "PROC. TIME 06:35—SCAN DATA," which message remains on the display until the operator scans all the data using scanner 112.

At this point, the tube 162 from needle 174 may be clamped using clamp 178, the needle 174 may be removed from the donor's arm A and a dressing applied to the puncture site. Also, the anticoagulant tube 152 may be clamped downstream from filter 154 using a hemostat (not shown).

When blood is drawn from a donor, the donor is required to fill out a registration form indicated at 196 at FIG. 4. The requested information for the form includes biographical information, prior medical history, allergic reactions and other conditions that could affect the quality of the donor's blood. Also, during or following the collection procedure, blood collected in the sample pouch 168 is often transferred to a plurality of sample tubes such as tubes 200a, 200b and 200c in FIG. 4 so that the blood sample can be subjected to various tests. That being the case, it is essential that the various disposable components of the blood collection system such as in blood bag 122 and the sample tubes 200a to 200c be correlated with the particular donor via his/her registration form 196 so that the drawn blood can be properly identified. To this end, the present system incorporates a labeling procedure which facilitates tracking the blood bags and sample tubes to avoid mis-identification of the drawn blood.

More particularly, when a donor fills out the registration form 196 and the blood collection set 12 is selected for that donor, a large label 202 may be adhered to the blood collection bag 122 of that set as shown in FIG. 4. That label carries a fixed bar code 204 as well as a plurality of removable bar code strips 206, each bearing the same code as strip 204. The strips 206 can be peeled away from label 202 and adhered to the donor's registration form 196 as well as to the pouch 160 and sample tubes 200a to 200c as shown in FIG. 4.

Preferably also, the sample tubes 200a to 200c carry fixed bar codes 208a, 208b and 208c which classify the tubes and/or identify the particular test that is to be performed on the blood sample in that tube.

Using scanner 112 of our system, an operator may scan the bar codes on blood bag 122, the donor registration form 206 and the sample tubes 200a to 200c into the memory of controller 26 so that the bar code numbers are stored in the memory. Thus, the memory contains the necessary data to correlate the blood bag and sample tubes with the particular donor registration form. Furthermore, scanning of the sample tube bar codes or identifiers 208a to 208c allows the system to store information about the count and type of tubes to ensure that all necessary tests are performed on the drawn sample of that particular donor's blood and to signal if there is no match. For example, controller 26 may contain a database relating different types of tests with the tubes (or other disposable items) associated with that test. Upon completion of the procedure, scanning of the fixed and donor bar codes on the tubes ensures that all necessary samples have been taken, and that the tubes all contain samples from the proper donor.

Following scanning, the controller 26 automatically activates printer 62 (FIG. 2) which thereupon prints a hard copy of all of the information stored in the controller 26 memory associated with the collection of that particular donor's blood, i.e., blood value, volume collected and process time. The data will also include the aforesaid identification numbers scanned into the memory by scanner 112. Inclusion of the identifiers in the stored data assures that when the blood collection bag 122 and sample tubes 200a to 200c are separated, they can still be correlated with the particular donor via his/her registration form 196 to provide positive collected product and sample identification. Of course, ensuring proper identification of collected blood requires recourse to the stored data, and is also assumes that scanning has been accomplished properly.

It is possible to add a second level of validation directly to the bag 122 itself by affixing thereto an additional bar code label that unambiguously identifies both the bag and the donor. For example, following scanning of the donor bar code 206 and bar code 204, printer 62 may be caused to print a master bar code label containing both bar code numbers; this label may be affixed to bag 122 and/or to the donor's registration form. In this way, the donor's identifier appears directly on bag 122, and mislabeling can be detected by scanning both bar codes now appearing on the bag (since the master bar code must contain the bar code originally appearing on bag 122).

Printer 62 may also print other information entered into or generated by the system such as time, date, procedure time, any procedural problems encountered, collected blood product volume, anticoagulant volume used for the particular collection, expiration date code for the anticoagulant and similar relevant information. Once again, this same information may be stored for each procedure in the controller 26 database, facilitating later retrieval and analysis. Thus, unit 10 constitutes both a data collector and a data tracker.

After the data has been printed out, display 96 will show the message "PROCEDURE COMPLETE," signaling that set 12 may be separated from the pump/control unit 10 by opening platen 32 and disconnecting the filter luer 146a from nipple 102a on unit 10 and removing bag 122 from hook 108. After the tubes 132 and 166 leading from bag 122 and pouch 168, respectively, have been sealed closed at the outlets from those bags, those tubes may be cut up from the seals to separate the bag and pouch from the remainder of set 12, which remainder may then be disposed of in accordance with accepted OSHA standards.

The procedure is more or less the same for the VOLUME and RED CELL modes of operation. In the former case, the collected product is a selected volume of anticoagulated whole blood. In the latter case, the collected product is a selected volume of anticoagulated blood based on the donor's hematocrit and a selected volume (e.g., 180 ml) of RBC. In both cases, the ratio of blood to anticoagulant is 8:1 as occurs when unit 10 is operating in its STANDARD mode and similar information is collected, displayed and printed out by printer 62.

Refer now to FIG. 5 which shows the pump 16 in greater detail. The pump may be accessed by removing a door 210 (FIGS. 1 and 5) in the sidewall of the pump housing 14. When door 210 is removed, the pump, which is attached to the door, disengages from the output shaft 22a of clutch 22 and slides out of the housing 14.

Pump 16 includes a housing 212 having a cylindrical neck 214 which slides over the output shaft 22a of clutch 22. Neck 214 has diametrically opposite slots 216 for receiving diametrically opposite pins 218 projecting out from the clutch shaft 22a. Therefore, when the collar is engaged to that shaft as shown in FIG. 5, it is rotatably fixed to the shaft.

The housing 212 rotatably supports the pump rollers 19 of pump head 16a by way of a circular array of axles 222. Housing 222 also has an axial opening for receiving a shaft 224. One end of the shaft extends through a bearing unit 226 at the base of neck 214 and is fixed axially by a C-clip 228. The shaft 224 extends all the way through housing 212 and out the opposite end of the housing which end is recessed at 230 for accommodating a relatively large gear 232 which is fixed to rotate with shaft 224. Also located in recess 230 is at least one relatively small diameter spur gear 234 which is rotatably mounted to one of the axles 222 so that it meshes with gear 232. A bearing unit 236 in recess 230 supports shaft 224 at its midpoint. Disposed radially outboard bearing 236 is a second relatively large gear 238 connected by fasteners 242 to the head 244a of a bushing 244 which is free to rotate on the shaft. The gear 238 also meshes with spur gear 234. In other words, that gear 234 meshes with both of the large gears 232 and 238. All of those gears comprise the speed reducer 24.

The pump head 16b comprises a spool 252 which encircles bushing 244. Preferably, a bearing element 254 is present between the spool and the bushing so that the spool can rotate freely. Preferably also, the bearing element 254 is a uni-directional bearing element so that the spool can only rotate in one direction on the bushing. As with housing 212, the spool 252 carries a circular array of axles 256 which rotatably support the rollers 19 of the pump head 16b.

Another bearing element 258 is recessed into the outer end of spool 252 so that the spool can rotate readily on shaft 224. The free end of the shaft projects beyond spool 252 in order to receive a sleeve 262 engaged onto the end of the shaft. That end of the shaft 224 is provided with flats 264 which interfit with sleeve 262 so that those two members are rotatably locked together. The end of sleeve 262 carries a key 262a which fits in a keyway 268 in the inside surface of door 210. The end of shaft 224 and sleeve 262 are positively connected to door 210 by means of a threaded fastener 270 which extends through axial holes in the door and sleeve and is turned down into a threaded hole in the end of shaft 224.

When pump 16 is in operation, shaft 224 is held stationary by door 210. Housing 212 is rotated by clutch 22 thereby rotating the pump head 16a. The gears 232, 234 and 238 in the speed reducer 24 effect a gear reduction as well as a motion reversal so that the spool 252 comprising the pump head 16b rotates in the opposite direction from the housing 212 in head 16a at a reduced speed, e.g., with a speed reduction ratio of 8:1. Because of the one-way clutching action incorporated into bearing element 254, the spool 252 will only be rotated in a direction which pumps anticoagulant from bag B (FIG. 1).

If it is desired to change the ratio of blood to anticoagulant in the blood being drawn by the present system, it is only necessary to substitute for the pump 16, a similar pump having a different gear reduction in the gear reducer 24.

While the illustrated pump 16 is designed so that the pump head 16a rotates in one direction and the pump head 16b rotates in the opposite direction, it should be understood that the gear reducer 24 can be designed with additional gears so that the two heads rotate in the same direction. In addition, the pump may incorporate more than two pump heads to pump fluids through several lines simultaneously at different rates. Furthermore, in some applications, it may be desirable to drive the pump with a bidirectional motor so that the pump head 16a which pumps blood product, can pump in both directions while the pump head 16b, due to the presence of the one-way clutch therein, can only rotate in one direction. Such an arrangement may be used for apheresis as described in the above U.S. Pat. No. 5,387,187.

Although the foregoing operations are representative of a typical blood-collection procedure, the invention may be employed for other types of procedures, or implemented to serve different functions. For example, the invention may be configured for surgical wound drainage rather than blood collection. In this application, controller 26 operates pump 16 to apply a constant negative pressure to a wound via a length of tubing. Blood is withdrawn and filtered in accordance with known autotransfusion procedures, and is typically returned to the patient.

It will thus be seen that the objects set forth above, among those made apparent from the preceding description, are efficiently attained and, since certain changes may be made in the above sequence of steps and in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Blood collection apparatus comprising
    a pump unit, said unit including
        a first pump head;
        a second pump head;
        a gear reducer rotatably coupling the first and second pump heads so that when one of said pump heads is rotated, both pump heads rotate with a selected speed ratio;
        motive means for rotating one of the pump heads, and
        means for releasably joining first and second tubes of a blood collection set in pumping relation with said first and second pump heads, respectively, so that when the tubes are joined with the pump heads and said motive means rotate said first pump head, fluid will flow through the first and second tubes at a volumetric ratio substantially equal to said speed ratio.

2. The apparatus defined in claim 1 wherein each pump head comprises a peristaltic pump which includes a plurality of rollers.

3. The apparatus defined in claim 2 wherein the joining means comprise a platen movable between a closed position wherein the platen is close to and opposite said pump heads and an open position wherein the platen is situated away from and exposes said pump heads.

4. The apparatus defined in claim 2 wherein the speed ratio is in excess of 5:1.

5. The apparatus defined in claim 2 wherein the gear reducer includes means for rotating the second pump head in a direction opposite to that of the first pump head.

6. The apparatus defined in claim 5 wherein said first and second pump heads are collinear.

7. The apparatus defined in claim 1 and further comprising a disposable blood collection set, said set including a phlebotomy needle;

a first flexible tube in fluid communication with said needle and having a segment thereof joined by said joining means with said first pump head, and a second flexible tube in fluid communication with said needle and having a segment thereof joined by said joining means with said second pump head.

8. The apparatus defined in claim 7 wherein the blood collection set also includes a tubing tray supporting said segments of said first and second tubes in spaced parallel relation opposite said first and second pump heads, respectively.

9. The apparatus defined in claim 8 wherein said tray is a card-like member having a relatively large opening which is bridged by said first and second tube segments.

10. The apparatus defined in claim 9 wherein said tray includes a window which is bridged by said second tube, and said pump unit includes a fluid flow detection means for detecting the presence or absence of fluid flowing through the second tube and producing a corresponding signal.

11. The apparatus defined in claim 10 wherein said unit further includes control means responsive to said signal for disabling said motive means when the detection means detects the absence of fluid for a selected number of revolutions of one of said pump heads.

12. Blood collection apparatus comprising a housing having a top wall with an opening therein;

first and second roller pump heads rotatably mounted in said housing, said pump heads being exposed in said opening;

a speed reducer coupling the first pump head to the second pump head so that when one of the pump heads is rotated, the two heads rotate with a selected speed ratio;

a platen movably mounted to said top wall adjacent to the opening therein, said platen being movable between a closed position wherein the platen is spaced opposite the pump heads and closes said opening and an open position wherein the platen is swung away from said opening thereby exposing said pump heads;

means for releasably maintaining the platen in its said closed position;

motive means in the housing for rotating one of the pump heads, and a programmable controller in the housing for controlling the motive means so that said one pump head is rotated at a selected speed within a selected speed range.

13. The apparatus defined in claim 12 wherein the first and second pump heads rotate in opposite directions.

14. The apparatus defined in claim 12 and further including a one-way clutch coupled to one of the pump heads so that said one pump head can only rotate in one direction.

15. The apparatus defined in claim 12 and further including a pressure transducer having a pressure inlet and positioned in the housing, said transducer producing an output indication to said controller indicative of the pressure at said inlet, said controller being programmed to control said motive means so that the speed of said first pump head varies within said range according to the pressure at said inlet.

16. The apparatus defined in claim 12 and further including means in said housing for sensing that the platen is in said closed position and providing an electrical indication to said controller in response thereto, said controller being programmed to disable said motive means in the absence of said indication.

17. The apparatus defined in claim 12 and further including fluid detection means mounted in said housing near said opening therein, said detection means producing an indication to said controller when it fails to detect fluid, said controller being programmed to disable said motive mean s when said fluid detector fails to detect fluid after a selected number of revolutions of said second pump head.

18. The apparatus defined in claim 17 where in the detection means comprises a first sonic emitter/detector, and further including a second sonic emitter/detector positioned in said platen which, when said platen is in its said closed position, is located directly opposite said first emitter detector.

19. The apparatus defined in claim 12 and further including a weigher associated with said housing and for supporting a blood collection bag, said weigher providing an output indication to said controller indicative of the bag weight, said controller being programmed to convert the weight indication to a bag contents volume indication and to turn off the motor when said volume indication reaches a target volume.

20. The apparatus defined in claim 19 and further including means for inputting data to said controller for changing said target volume.

21. The apparatus defined in claim 12 and further comprising a disposable blood collection set, said set including a blood collection bag;

a first tube leading to said bag;

a second tube having one end in fluid communication with the first tube and having a second end adapted to be connected to a source of anticoagulant;

a tubing tray, said tray having an opening therethrough;

means for securing said first and second tubes to the tray so that segments of said tubes are maintained in spaced relation opposite said opening, said tray being positioned on the top wall of said housing when said platen is in its open position so that said tray opening is located opposite the wall opening and so that when the platen is moved to its closed position, the tube segments are captured between the platen and the first and second pump heads.

22. The apparatus defined in claim 21 and further including fluid detection means mounted in the housing top wall adjacent to the opening therein, and a window in said tray opposite said detection means which exposes a portion of the second tube to said detection means.

23. The apparatus defined in claim 21 and further including a coded label affixed to said blood collection bag for being correlated with a coded sticker affixed to a donor registration form for tracking purposes.

24. The apparatus defined in claim 23 and further including a database associated with the controller for storing data including identifiers, and means for acquiring a donor identifier corresponding to a particular blood donor and adding it to the database, and means for scanning said set identifier and inputting the scanned data into the database whereby said blood collection set can be correlated with that particular blood donor.

25. The apparatus defined in claim 24 and further including a printer in the housing for printing out data stored in said database.

26. The apparatus defined in claim 12 and further including a one-way clutch coupled to each of said pump heads so that each of said pump heads can only rotate in a selected direction.

* * * * *